US012622663B2

(12) United States Patent
Anzai et al.

(10) Patent No.: US 12,622,663 B2
(45) Date of Patent: May 12, 2026

(54) STANDARD BLOOD VESSEL GENERATION DEVICE, BLOOD VESSEL EVALUATION DEVICE, STANDARD BLOOD VESSEL GENERATION PROGRAM, BLOOD VESSEL EVALUATION PROGRAM, STANDARD BLOOD VESSEL GENERATION METHOD, AND BLOOD VESSEL EVALUATION METHOD

(71) Applicant: TOHOKU UNIVERSITY, Sendai (JP)

(72) Inventors: Hitomi Anzai, Sendai (JP); Ko Kitamura, Sendai (JP); Shunji Mugikura, Sendai (JP); Naoko Mori, Sendai (JP); Makoto Ohta, Sendai (JP)

(73) Assignee: TOHOKU UNIVERSITY, Sendai (JP)

( * ) Notice: Subject to any disclaimer, the term of this patent is extended or adjusted under 35 U.S.C. 154(b) by 550 days.

(21) Appl. No.: 18/008,569

(22) PCT Filed: Jun. 9, 2021

(86) PCT No.: PCT/JP2021/021889
§ 371 (c)(1),
(2) Date: Dec. 6, 2022

(87) PCT Pub. No.: WO2021/251425
PCT Pub. Date: Dec. 16, 2021

(65) Prior Publication Data
US 2023/0225691 A1     Jul. 20, 2023

(30) Foreign Application Priority Data
Jun. 9, 2020    (JP) ................................. 2020-100391

(51) Int. Cl.
*A61B 6/50*        (2024.01)
*A61B 5/00*        (2006.01)
(Continued)

(52) U.S. Cl.
CPC ................ *A61B 6/504* (2013.01); *A61B 5/00* (2013.01); *A61B 6/48* (2013.01); *A61B 6/5217* (2013.01);
(Continued)

(58) Field of Classification Search
CPC ........... A61B 6/504; A61B 6/48; A61B 6/032; A61B 5/00; A61B 5/055; A61B 6/5217;
(Continued)

(56) References Cited

U.S. PATENT DOCUMENTS

| | | | |
|---|---|---|---|
| 2012/0014574 A1* | 1/2012 | Ferschel | G06T 7/0012 |
| | | | 382/128 |
| 2013/0009958 A1* | 1/2013 | Kitamura | A61B 6/032 |
| | | | 345/424 |

(Continued)

FOREIGN PATENT DOCUMENTS

| | | | | |
|---|---|---|---|---|
| CN | 111161342 A | * | 5/2020 | G06T 17/00 |
| JP | A-08-280655 | | 10/1996 | |

(Continued)

OTHER PUBLICATIONS

PCT International Search Report (w/ English translation) and Written Opinion for corresponding PCT Application No. PCT/JP2021/021889, mailed on Aug. 3, 2021, 10 pages.

(Continued)

*Primary Examiner* — John Villecco
*Assistant Examiner* — Joshua B. Crockett
(74) *Attorney, Agent, or Firm* — Dority & Manning, P.A.

(57) ABSTRACT

A standard blood vessel generation device specifies, for each subject, a blood vessel region in which a blood vessel is depicted in an image, derives a feature line that connects feature points included in a plurality of figures included in the blood vessel region and that is along the blood vessel region, specifies a branch point on the feature line, disposes (Continued)

division points for line division on a line with a start point being one of two adjacent branch points and an end point being the other branch point, executes, for each set of division points having the same order counted from the start point in a plurality of the subjects, a process of calculating a statistic amount of coordinates for the set of the division points and setting a point whose coordinates are equal to the statistic amount as a standard point, and a process of setting a dimension of a predetermined site in the figure including the standard point and included in the blood vessel region as a standard diameter, and generates a standard blood vessel that is a blood vessel whose diameter at the standard point is the standard diameter and that is along a standard line connecting a plurality of the standard points.

12 Claims, 15 Drawing Sheets

(51) Int. Cl.

| | |
|---|---|
| *A61B 6/00* | (2024.01) |
| *G06T 7/00* | (2017.01) |
| *G06T 7/12* | (2017.01) |
| *G06T 7/62* | (2017.01) |
| *A61B 5/02* | (2006.01) |
| *A61B 5/055* | (2006.01) |
| *A61B 8/08* | (2006.01) |
| *G06T 7/11* | (2017.01) |

(52) U.S. Cl.
CPC .......... *G06T 7/0012* (2013.01); *G06T 7/0014* (2013.01); *G06T 7/62* (2017.01); *A61B 5/02007* (2013.01); *A61B 5/055* (2013.01); *A61B 8/0891* (2013.01); *G06T 7/11* (2017.01); *G06T 7/12* (2017.01); *G06T 2207/10081* (2013.01); *G06T 2207/10088* (2013.01); *G06T 2207/30016* (2013.01); *G06T 2207/30101* (2013.01); *G06T 2207/30172* (2013.01)

(58) Field of Classification Search
CPC .............. A61B 5/02007; A61B 8/0891; G06T 2207/30101; G06T 7/0014; G06T 7/12; G06T 2207/10081; G06T 2207/10088; G06T 2207/30016; G06T 2207/30172; G06T 7/11; G06T 7/0012; G06T 7/60; G06T 7/62
See application file for complete search history.

(56) References Cited

U.S. PATENT DOCUMENTS

| | | | | |
|---|---|---|---|---|
| 2020/0357162 A1* | 11/2020 | Li | ........................ | A61B 6/5247 |
| 2022/0028077 A1* | 1/2022 | Seo | ........................ | G06T 7/0014 |
| 2022/0192617 A1* | 6/2022 | Wang | ...................... | G06T 7/136 |

FOREIGN PATENT DOCUMENTS

| | | | | |
|---|---|---|---|---|
| JP | A-2005-518893 | 6/2005 | | |
| JP | A-2009-011828 | 1/2009 | | |
| JP | A-2009-268741 | 11/2009 | | |
| JP | A-2010-131257 | 6/2010 | | |
| WO | WO 2017/047819 | 3/2017 | | |
| WO | WO-2017047819 A1 * | 3/2017 | .............. | A61B 6/03 |

OTHER PUBLICATIONS

Ko Kitamura et al., "3D Structure Standardization of Cerebral Artery Using MRA Images for Classificattion," 6th International Conference on Computational and Mathematical Biomedical Engineering-CMBE2019, vol. 2, pp. 491-493, Jun. 10, 2019.

* cited by examiner

[FIG. 1]
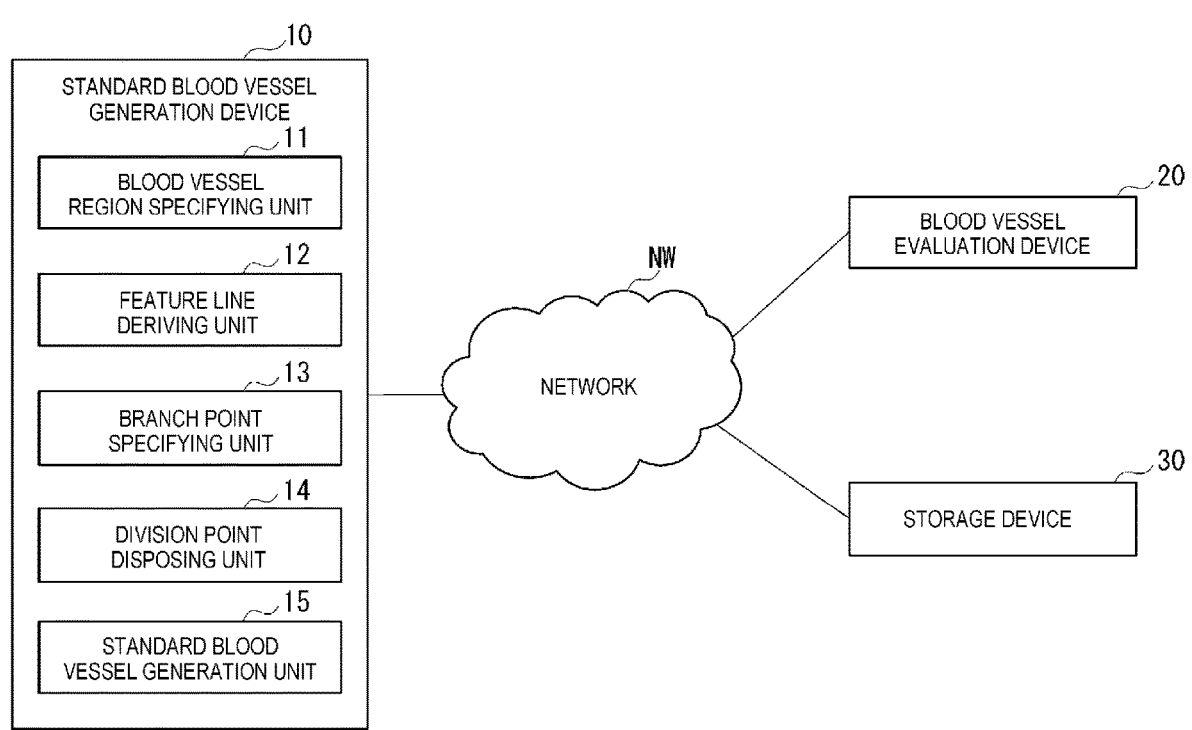

[FIG. 2]
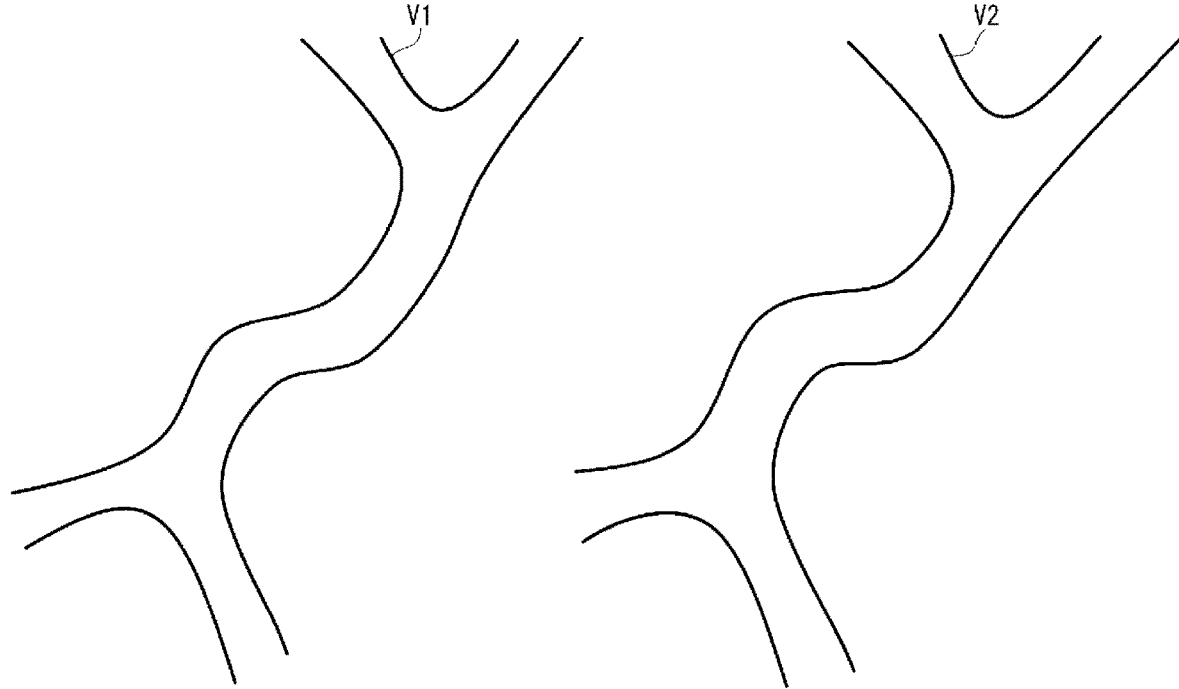

[FIG. 3]
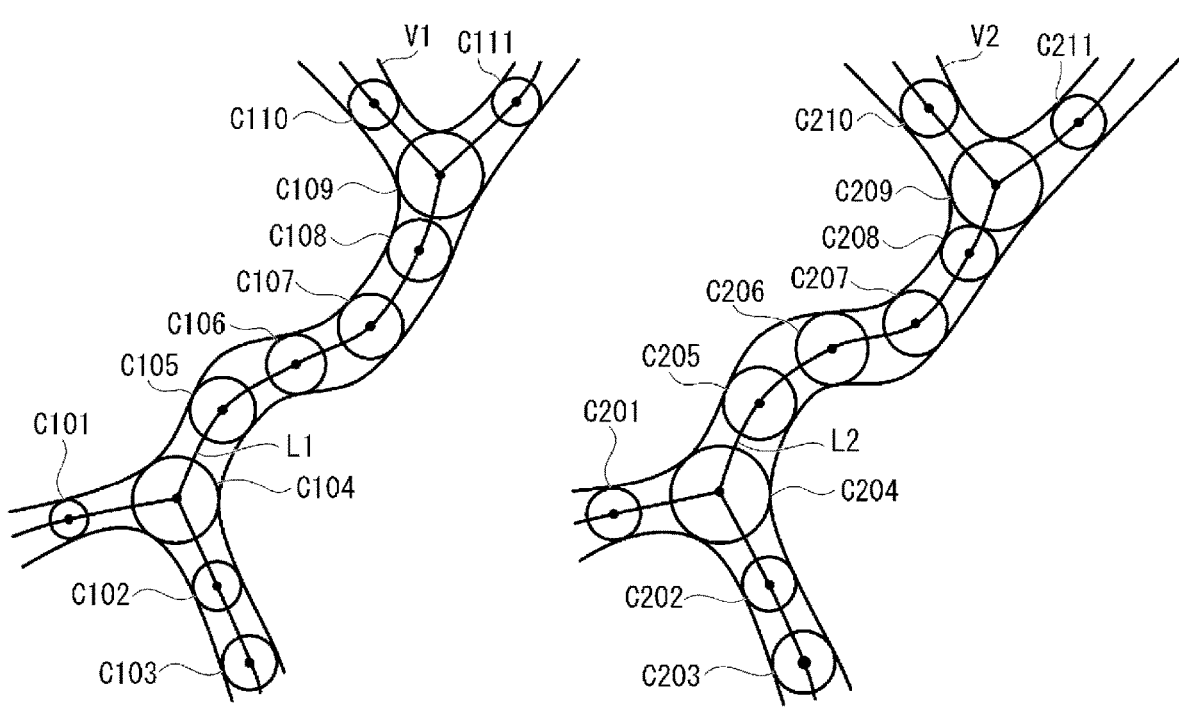

[FIG. 4]
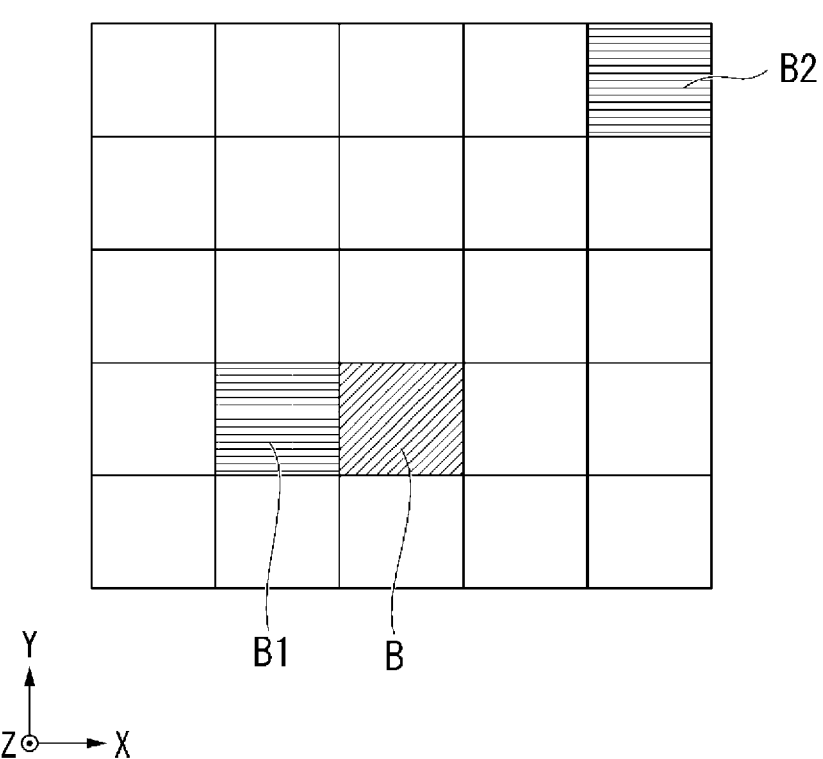

[FIG. 5]
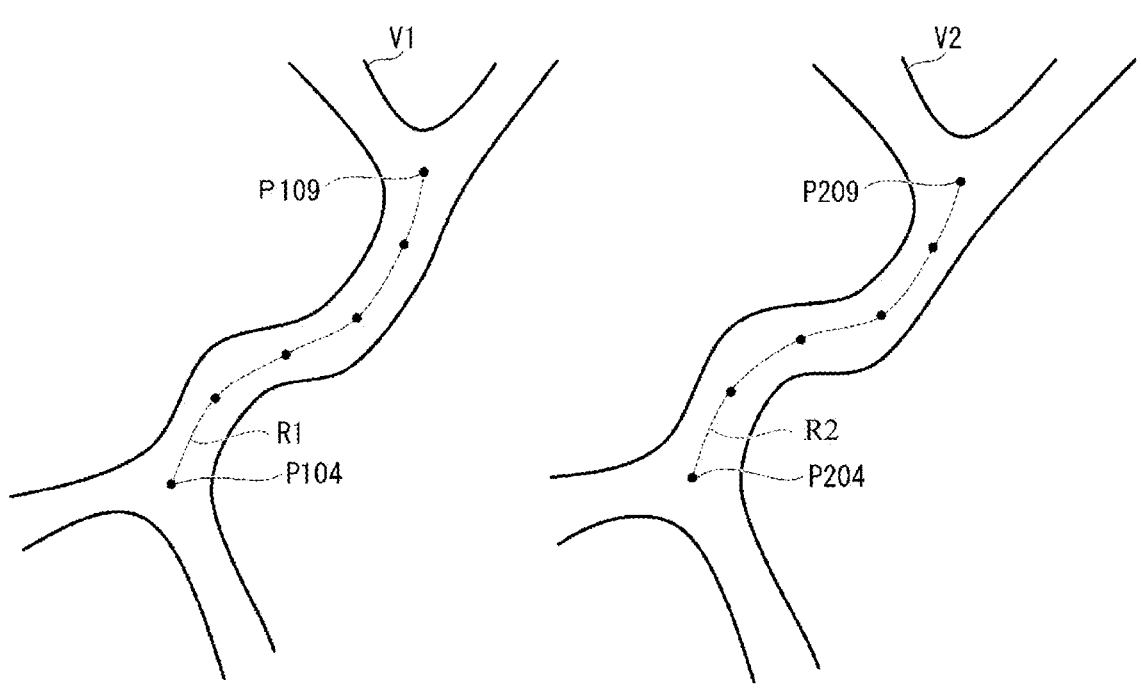

[FIG. 6]
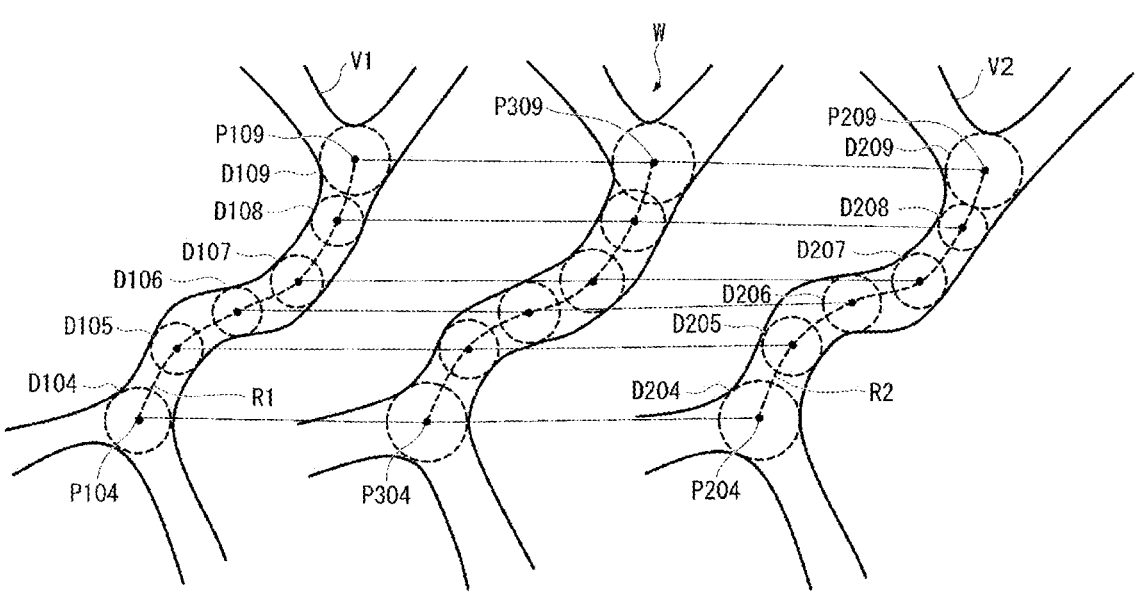

[FIG. 7]
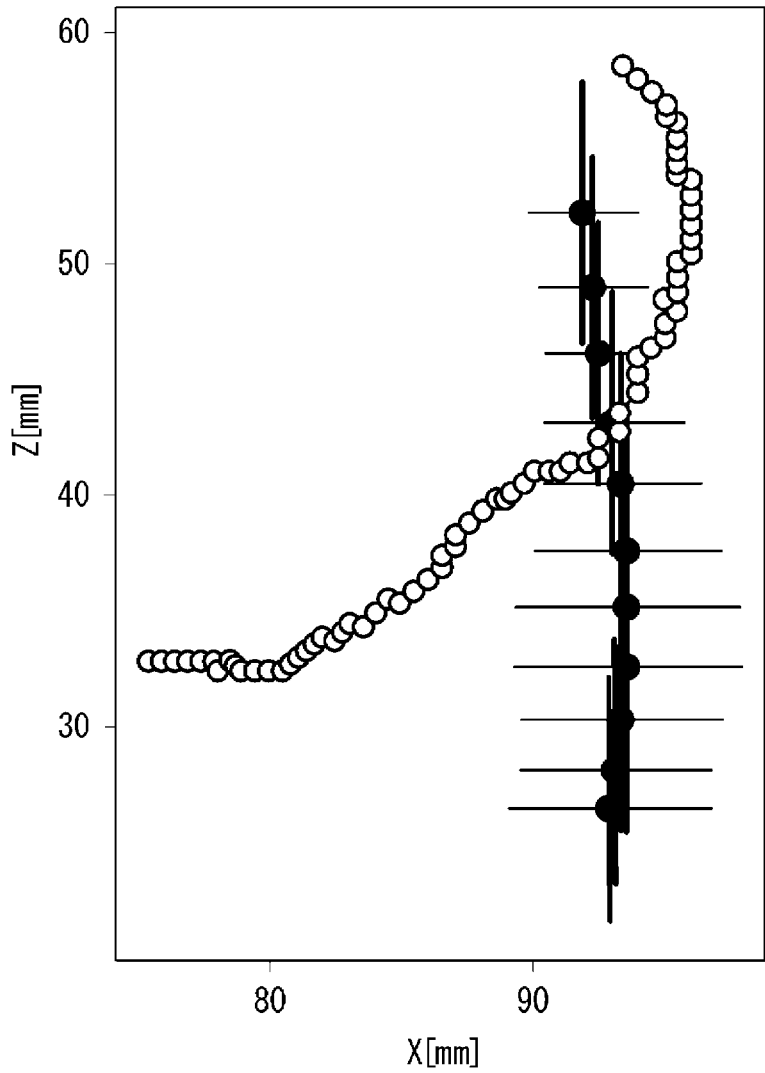

[FIG. 8]
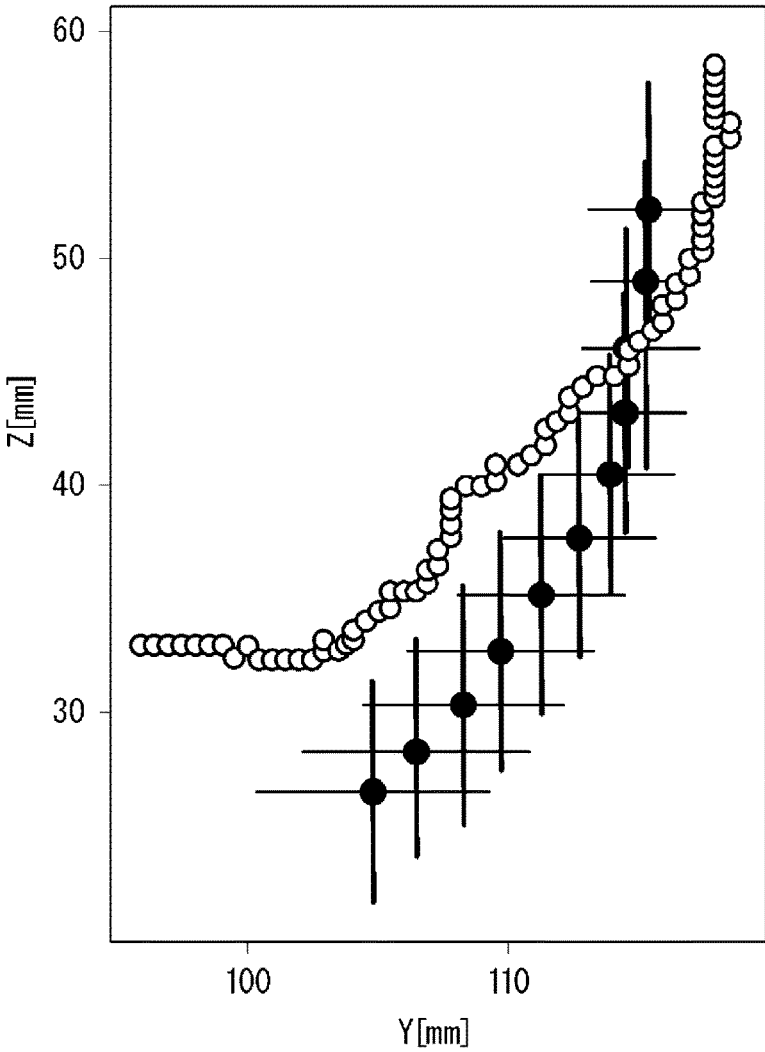
[FIG. 9]
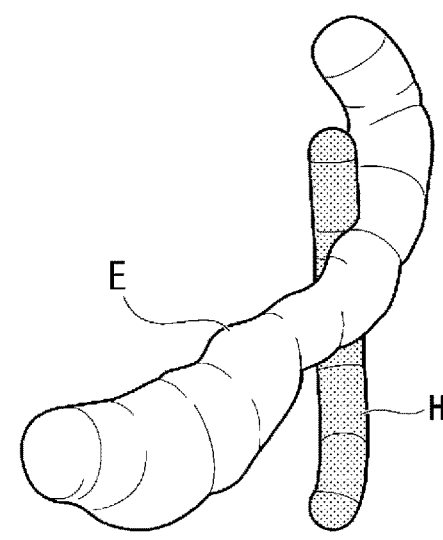

[FIG. 10]
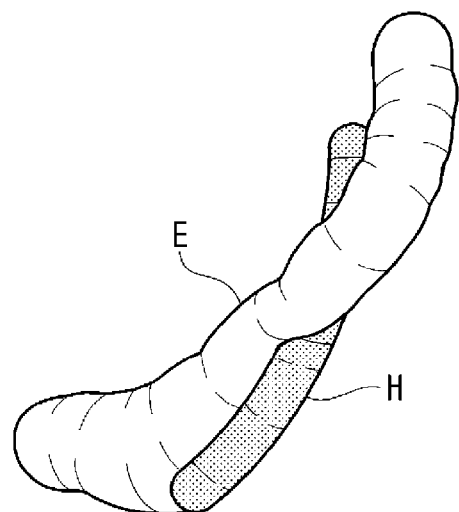

[FIG. 11]
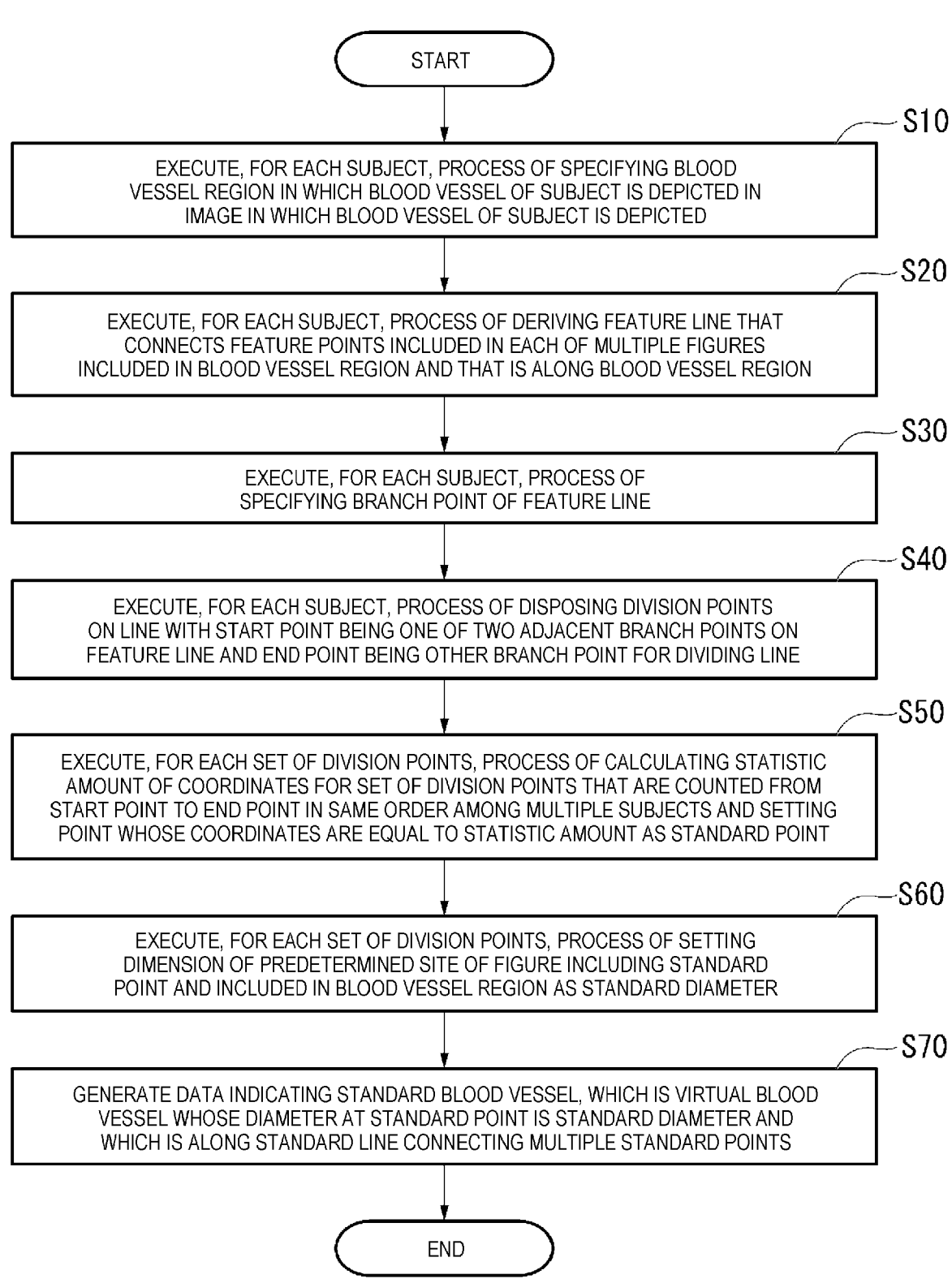

[FIG. 12]
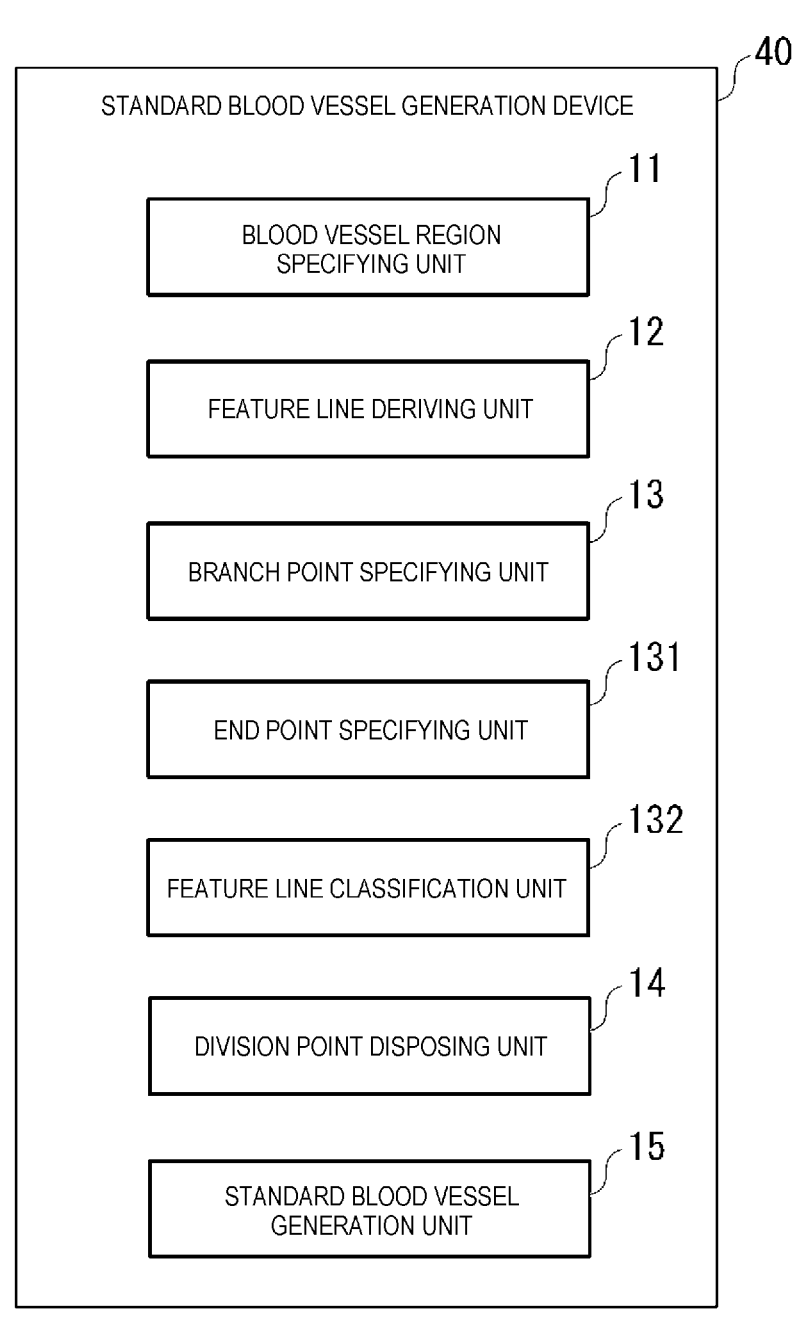

[FIG. 13]
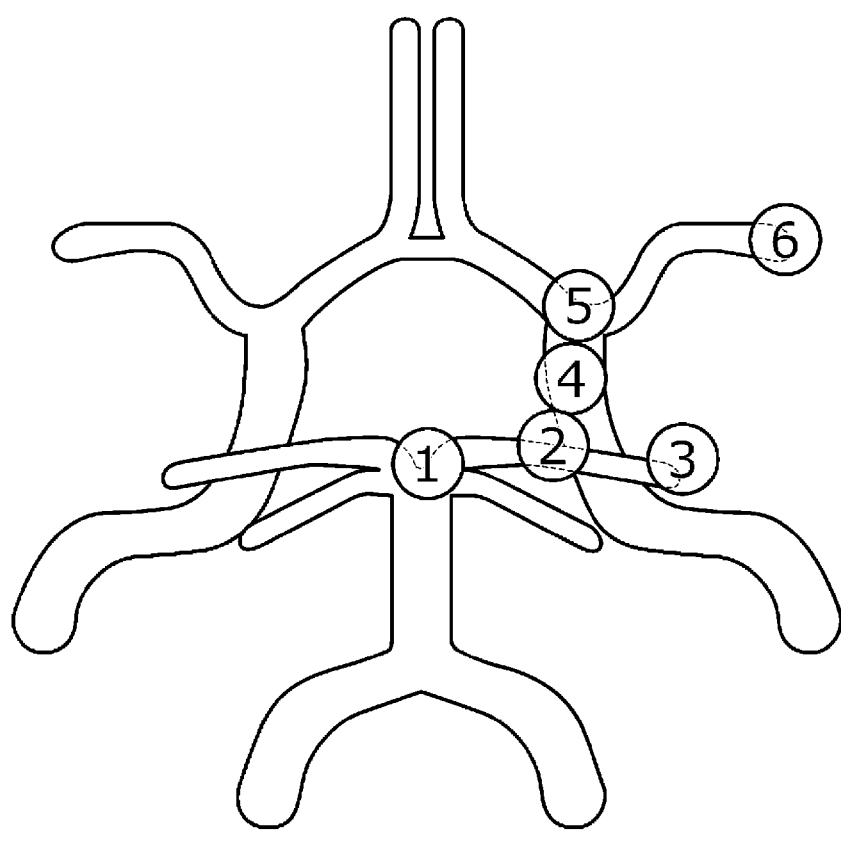
[FIG. 14]
|   | 1 | 2 | 3 | 4 | 5 | 6 |
|---|---|---|---|---|---|---|
| 1 | ▨ |   | ○ |   |   |   |
| 2 | ▨ | ▨ |   |   |   |   |
| 3 | ▨ | ▨ | ▨ |   |   |   |
| 4 | ▨ | ▨ | ▨ | ▨ |   |   |
| 5 | ▨ | ▨ | ▨ | ▨ | ▨ | ○ |
| 6 | ▨ | ▨ | ▨ | ▨ | ▨ | ▨ |

[FIG. 15]
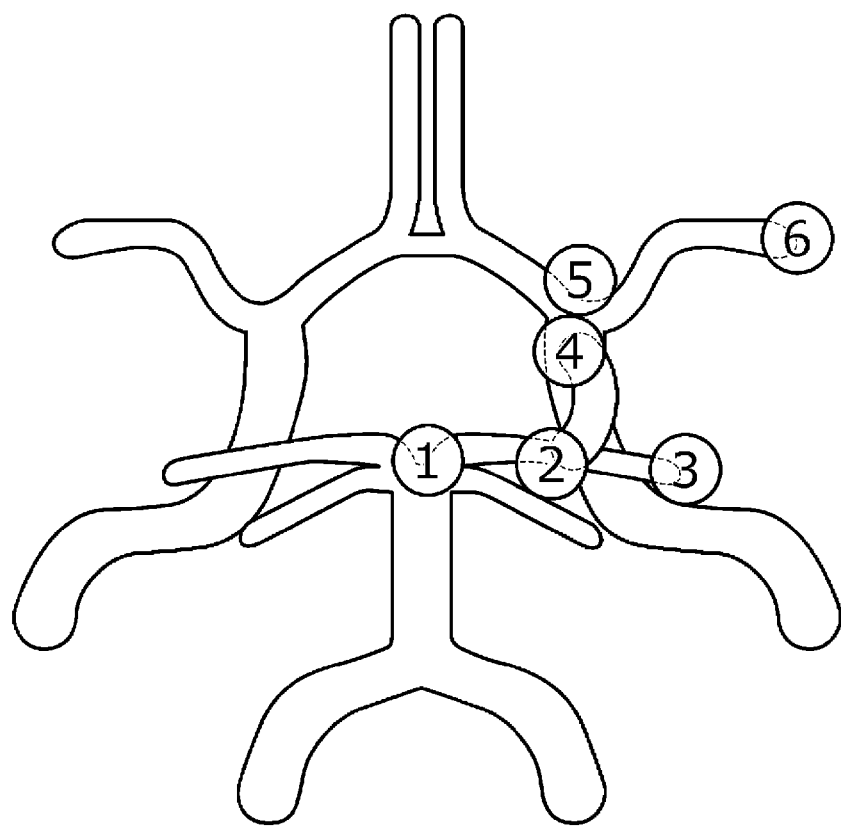
[FIG. 16]
|   | 1 | 2 | 3 | 4 | 5 | 6 |
|---|---|---|---|---|---|---|
| 1 | ▨ | ◯ |   |   |   |   |
| 2 | ▨ | ▨ | ◯ | ◯ |   |   |
| 3 | ▨ | ▨ | ▨ |   |   |   |
| 4 | ▨ | ▨ | ▨ | ▨ | ◯ |   |
| 5 | ▨ | ▨ | ▨ | ▨ | ▨ | ◯ |
| 6 | ▨ | ▨ | ▨ | ▨ | ▨ | ▨ |

[FIG. 17]
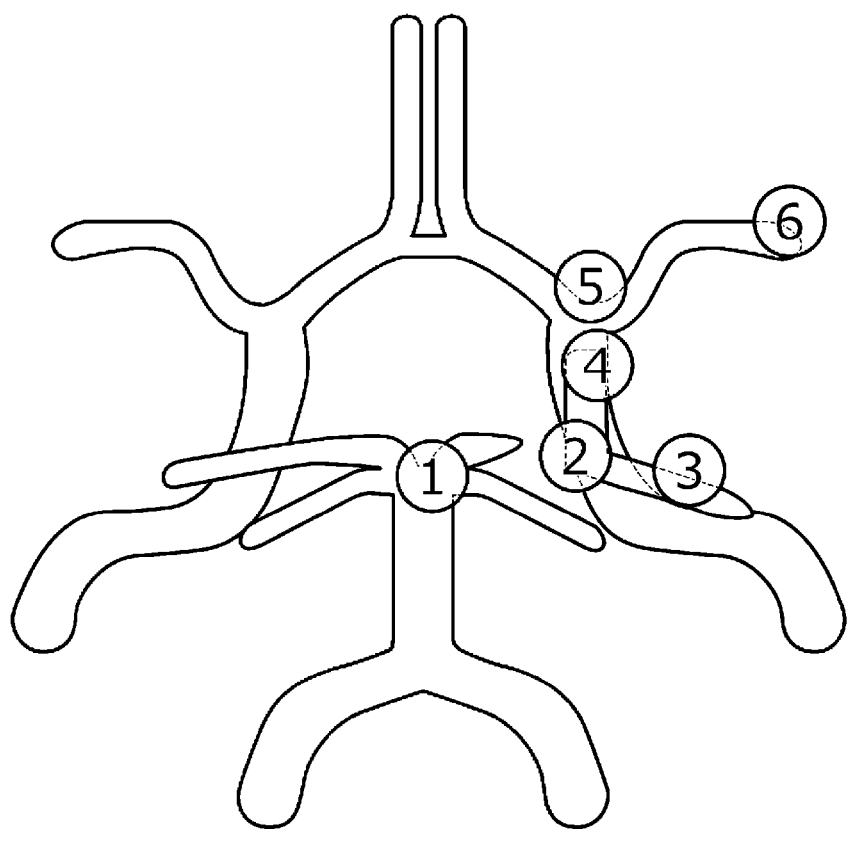
[FIG. 18]
|   | 1 | 2 | 3 | 4 | 5 | 6 |
|---|---|---|---|---|---|---|
| 1 | ▨ |   |   |   |   |   |
| 2 | ▨ | ▨ |   |   |   |   |
| 3 | ▨ | ▨ | ▨ | ○ |   |   |
| 4 | ▨ | ▨ | ▨ | ▨ | ○ |   |
| 5 | ▨ | ▨ | ▨ | ▨ | ▨ | ○ |
| 6 | ▨ | ▨ | ▨ | ▨ | ▨ | ▨ |

[FIG. 19]
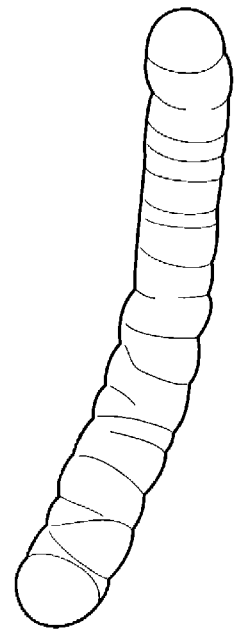
[FIG. 20]
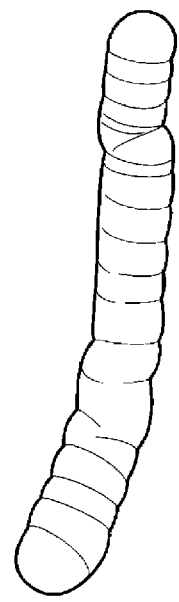

STANDARD BLOOD VESSEL GENERATION DEVICE, BLOOD VESSEL EVALUATION DEVICE, STANDARD BLOOD VESSEL GENERATION PROGRAM, BLOOD VESSEL EVALUATION PROGRAM, STANDARD BLOOD VESSEL GENERATION METHOD, AND BLOOD VESSEL EVALUATION METHOD

CROSS REFERENCE TO RELATED APPLICATIONS

This application is the U.S. National Stage entry of International Application No. PCT/JP2021/021889 filed under the Patent Cooperation Treaty on Jun. 9, 2021, which claims priority to Japanese Patent Application No. 2020-100391 filed on Jun. 9, 2020, both of which are incorporated herein by reference.

TECHNICAL FIELD

The present invention relates to a standard blood vessel generation device, a blood vessel evaluation device, a standard blood vessel generation program, a blood vessel evaluation program, a standard blood vessel generation method, and a blood vessel evaluation method.

BACKGROUND ART

In the related art, it has been pointed out that there is a disease that changes a shape of a blood vessel, a disease caused by a change in blood flow due to a change in a shape of a blood vessel, and the like. A technique for quantitatively evaluating a shape of a blood vessel is required to advance diagnosis, prevention, research, and the like of these diseases. An example of such a technique is a quantitative analysis apparatus for a blood vessel image disclosed in PTL 1.

The quantitative analysis apparatus for a blood vessel image includes a designation unit, a division unit, a profile direction determination unit, an edge extraction unit, a center line determination unit, and an analysis unit. The designation unit designates a blood vessel to be analyzed on the blood vessel image. The division unit divides a blood vessel into a plurality of parts. The profile direction determination unit determines a profile direction based on position information on the divided blood vessel. The edge extraction unit extracts a blood vessel edge of the blood vessel to be analyzed based on the profile direction determined by the profile direction determination unit. The center line determination unit determines a center line from the blood vessel edge extracted by the edge extraction unit. The analysis unit performs a quantitative analysis of the blood vessel to be analyzed based on data of the blood vessel edge extracted by the edge extraction unit and the center line determined by the center line determination unit.

CITATION LIST

Patent Literature

PTL 1: JP-A-08-280655

However, the quantitative analysis apparatus for a blood vessel image can specify a blood vessel image of an object, but cannot specify a degree of deviation of a shape of a blood vessel of the object from a shape of a blood vessel of a healthy person. In addition, since there is a personal difference in a shape of a blood vessel, it is necessary to determine the blood vessel of the healthy person that can be a reference in specifying the degree, but the quantitative analysis apparatus for a blood vessel image does not specify the blood vessel image of the object by using such a reference.

SUMMARY OF INVENTION

Technical Problem

Therefore, an object of the invention is to provide a standard blood vessel generation device, a standard blood vessel generation program, and a standard blood vessel generation method that can generate a standard blood vessel, which is a reference blood vessel suitable for specifying a shape of a blood vessel, and to provide a blood vessel evaluation device, a blood vessel evaluation program, and a blood vessel evaluation method that can more accurately evaluate a shape of a blood vessel of an object using the standard blood vessel.

Solution to Problem

A standard blood vessel generation device according to one aspect of the invention includes: a blood vessel region specifying unit configured to execute, for each subject, a process of specifying a blood vessel region in which a blood vessel of the subject is depicted in an image in which the blood vessel of the subject is depicted; a feature line deriving unit configured to execute, for each subject, a process of deriving a feature line that connects feature points included in each of a plurality of figures included in the blood vessel region and that is along the blood vessel region; a branch point specifying unit configured to execute, for each subject, a process of specifying a branch point of the feature line; a division point disposing unit configured to execute, for each subject, a process of disposing division points for line division on a line with a start point being one of two adjacent branch points on the feature line and an end point being the other branch point; and a standard blood vessel generation unit configured to execute, for each set of the division points, a process of calculating a statistic amount of coordinates for the set of the division points having the same order counted from the start point to the end point in a plurality of the subjects and setting a point whose coordinates are equal to the statistic amount as a standard point, and a process of setting a dimension of a predetermined site in the figure including the standard point and included in the blood vessel region as a standard diameter, and generate data indicating a standard blood vessel that is a virtual blood vessel whose diameter at the standard point is the standard diameter and that is along a standard line connecting a plurality of the standard points.

In the standard blood vessel generation device, the blood vessel region specifying unit may execute the process of specifying the blood vessel region in which the blood vessel of the subject is depicted in the image subjected to registration with respect to a reference image having a reference coordinate system.

In the standard blood vessel generation device, the feature line deriving unit may execute the process of deriving the feature line connecting centers of a plurality of spheres inscribed in the blood vessel region.

In the standard blood vessel generation device, the division point disposing unit may execute the process of disposing the division points on the line for equally dividing the line.

In the standard blood vessel generation device, the standard blood vessel generation unit may generate, as the standard blood vessel, the data indicating the virtual blood vessel having the diameter at the standard point equal to a diameter of a sphere inscribed in the blood vessel region.

The standard blood vessel generation device further includes a feature line classification unit configured to execute, for each subject, a process of determining a category to which a connection structure of the feature line depicted in the image belongs, based on a connection relation between the branch points on the feature line, the division point disposing unit is configured to execute the process of disposing the division points on the line for at least two blood vessels determined to belong to the same category by the feature line classification unit, and the standard blood vessel generation unit is configured to execute the process of generating the data indicating the standard blood vessel based on at least two blood vessels determined to belong to the same category by the feature line classification unit.

The standard blood vessel generation device further includes an end point specifying unit configured to execute, for each subject, a process of specifying an end point of the feature line, and the feature line classification unit is configured to execute, for each subject, the process of determining the category to which the blood vessel depicted in the image belongs, based on a connection relation between the end point and the feature point on the feature line.

In a blood vessel evaluation device according to one aspect of the invention, a blood vessel of an object is evaluated based on a standard blood vessel determined by a standard line that is included in an image in which a blood vessel of a subject is depicted and that is along a blood vessel region in which the blood vessel of the subject is depicted and a standard diameter that is a dimension of a predetermined site in each of a plurality of figures including points on the standard line and included in the blood vessel region.

A standard blood vessel generation program according to one aspect of the invention causes a computer to implement: a blood vessel region specifying function for executing, for each subject, a process of specifying a blood vessel region in which a blood vessel of the subject is depicted in an image in which the blood vessel of the subject is depicted; a feature line deriving function for executing, for each subject, a process of deriving a feature line that connects feature points included in each of a plurality of figures included in the blood vessel region and that is along the blood vessel region; a branch point specifying function for executing, for each subject, a process of specifying a branch point of the feature line; a division point disposing function for executing, for each subject, a process of disposing division points for line division on a line with a start point being one of two adjacent branch points on the feature line and an end point being the other branch point; and a standard blood vessel generation function for executing, for each set of the division points, a process of calculating a statistic amount of coordinates for the set of the division points having the same order counted from the start point to the end point in a plurality of the subjects and setting a point whose coordinates are equal to the statistic amount as a standard point, and a process of setting a dimension of a predetermined site in the figure including the standard point and included in the blood vessel region as a standard diameter, and generating data indicating a standard blood vessel that is a virtual blood vessel whose diameter at the standard point is the standard diameter and that is along a standard line connecting a plurality of the standard points.

In a blood vessel evaluation program according to one aspect of the invention, a blood vessel of an object is evaluated based on a standard blood vessel determined by a standard line that is included in an image in which a blood vessel of a subject is depicted and that is along a blood vessel region in which the blood vessel of the subject is depicted and a standard diameter that is a dimension of a predetermined site in each of a plurality of figures including points on the standard line and included in the blood vessel region.

A standard blood vessel generation method according to one aspect of the invention includes: a blood vessel region specifying step of executing, for each subject, a process of specifying a blood vessel region in which a blood vessel of the subject is depicted in an image in which the blood vessel of the subject is depicted; a feature line deriving step of executing, for each subject, a process of deriving a feature line that connects feature points included in each of a plurality of figures included in the blood vessel region and that is along the blood vessel region; a branch point specifying step of executing, for each subject, a process of specifying a branch point of the feature line; a division point disposing step of executing, for each subject, a process of disposing division points for line division on a line with a start point being one of two adjacent branch points on the feature line and an end point being the other branch point; and a standard blood vessel generation step of executing, for each set of the division points, a process of calculating a statistic amount of coordinates for the set of the division points having the same order counted from the start point to the end point in a plurality of the subjects and setting a point whose coordinates are equal to the statistic amount as a standard point, and a process of setting a dimension of a predetermined site in the figure including the standard point and included in the blood vessel region as a standard diameter, and generating data indicating a standard blood vessel that is a virtual blood vessel whose diameter at the standard point is the standard diameter and that is along a standard line connecting a plurality of the standard points.

In a blood vessel evaluation method according to one aspect of the invention, a blood vessel of an object is evaluated based on a standard blood vessel determined by a standard line that is included in an image in which a blood vessel of a subject is depicted and that is along a blood vessel region in which the blood vessel of the subject is depicted and a standard diameter that is a dimension of a predetermined site in each of a plurality of figures including points on the standard line and included in the blood vessel region.

Advantageous Effect

According to the invention, it is possible to generate a standard blood vessel, which is a reference blood vessel suitable for specifying a shape of a blood vessel, and to evaluate a shape of a blood vessel of an object more accurately using the standard blood vessel.

BRIEF DESCRIPTION OF DRAWINGS

FIG. 1 is a diagram showing an example of a functional configuration of a standard blood vessel generation device and a blood vessel evaluation device according to an embodiment of the invention.

FIG. 2 is a diagram showing an example of a blood vessel region according to the embodiment of the invention.

FIG. 3 is a diagram showing an example of a plurality of spheres inscribed in the blood vessel region and a feature line connecting centers of the spheres according to the embodiment of the invention.

FIG. 4 is a diagram illustrating an example of values assigned to branch point candidates according to the embodiment of the invention.

FIG. 5 is a diagram showing an example of two branch points, a line connecting the two branch points, a plurality of division points disposed on the line, and spheres centered at these respective division points and inscribed in the blood vessel region according to the embodiment of the invention.

FIG. 6 is a diagram showing an example of a standard blood vessel according to the embodiment of the invention.

FIG. 7 is a diagram showing an example of results of evaluating a center line of an internal carotid artery of an object suffering from a dolicoectasia and a center line of an internal carotid artery of a healthy object in a coronal plane by the blood vessel evaluation device according to the embodiment of the invention.

FIG. 8 is a diagram showing an example of results of evaluating the center line of the internal carotid artery of the object suffering from the dolicoectasia and the center line of the internal carotid artery of the healthy object in a sagittal plane by the blood vessel evaluation device according to the embodiment of the invention.

FIG. 9 is a diagram showing an example of results of evaluating a diameter of the internal carotid artery of the object suffering from the dolicoectasia and a diameter of the internal carotid artery of the healthy object by the blood vessel evaluation device when viewed from a direction perpendicular to the coronal plane according to the embodiment of the invention.

FIG. 10 is a diagram showing an example of results of evaluating the diameter of the internal carotid artery of the object suffering from the dolicoectasia and the diameter of the internal carotid artery of the healthy object by the blood vessel evaluation device when viewed from a direction perpendicular to the sagittal plane according to the embodiment of the invention.

FIG. 11 is a flowchart illustrating an example of a process executed by the standard blood vessel generation device according to the embodiment of the invention.

FIG. 12 is a diagram showing an example of a functional configuration of a standard blood vessel generation device according to another embodiment of the invention.

FIG. 13 is a diagram showing an example of a blood vessel according to the other embodiment of the invention.

FIG. 14 is a diagram showing an example of a matrix indicating a connection relation between branch points and end points on a feature line of the blood vessel shown in FIG. 13.

FIG. 15 is a diagram showing an example of a blood vessel according to the other embodiment of the invention.

FIG. 16 is a diagram showing an example of a matrix indicating a connection relation between branch points and end points on a feature line of the blood vessel shown in FIG. 15.

FIG. 17 is a diagram showing an example of a blood vessel according to the other embodiment of the invention.

FIG. 18 is a diagram showing an example of a matrix indicating a connection relation between branch points and end points on a feature line of the blood vessel shown in FIG. 17.

FIG. 19 is a diagram showing an example of a standard blood vessel generated by the standard blood vessel generation device based on blood vessels of a plurality of subjects classified into a left and right independent type when a posterior communicating artery is considered according to the other embodiment of the invention.

FIG. 20 is a diagram showing an example of a standard blood vessel generated by the standard blood vessel generation device based on blood vessels of a plurality of subjects classified into a left and right coupled type when the posterior communicating artery is considered according to the other embodiment of the invention.

DESCRIPTION OF EMBODIMENTS

An example of a standard blood vessel generation device and a blood vessel evaluation device according to an embodiment will be described with reference to FIGS. 1 to 10, FIG. 1 is a diagram showing an example of a functional configuration of the standard blood vessel generation device and the blood vessel evaluation device according to the embodiment of the invention. FIG. 1 shows a standard blood vessel generation device 10, a blood vessel evaluation device 20, and a storage device 30. The standard blood vessel generation device 10, the blood vessel evaluation device 20, and the storage device 30 are connected to one another via a network NW so as to be able to communicate with one another. The network NW is, for example, an intranet, a local area network (LAN), the Internet, or a wide area network (WAN).

As shown in FIG. 1, the standard blood vessel generation device 10 includes a blood vessel region specifying unit 11, a feature line deriving unit 12, a branch point specifying unit 13, a division point disposing unit 14, and a standard blood vessel generation unit 15.

The blood vessel region specifying unit 11 executes, for each subject, a process of specifying a blood vessel region in which a blood vessel of the subject is depicted in an image in which the blood vessel of the subject is depicted. The subject referred to here is a part of a body of a person depicted in a medical image to be used for generating data indicating a standard blood vessel to be described later by the standard blood vessel generation device 10. In the following description, a case in which the subject is a human head and the blood vessel is an artery in a brain will be described as an example.

The medical image is, for example, a magnetic resonance angiography (MRA) image captured by an angiography examination using a magnetic resonance imaging (MRI) apparatus. Alternatively, the medical image is a computed tomography angiography (CTA) image captured by an examination using a computed tomography (CT) apparatus. Alternatively, the medical image is an angiography image using a blood vessel imaging apparatus, or an ultrasonic image captured by an examination using an ultrasonic diagnostic apparatus. In addition, it is preferable that these medical images three-dimensionally depict the blood vessel of the subject and the periphery of the blood vessel. However, these medical images may two-dimensionally depict the blood vessel of the subject and the periphery of the blood vessel.

It is preferable that a blood vessel region specifying unit executes a process of specifying a blood vessel region in which a blood vessel of a subject is depicted in an image subjected to registration with respect to a reference image having a reference coordinate system. The registration referred to here is a process in which a target image that is the image in which the subject is depicted is subjected to linear conversion or non-linear conversion, and the target image is adjusted to the same coordinate system as that of the reference image by reducing a residual function between the target image and the reference image as much as possible.

The linear conversion is a process of deforming at least a part of the target image by applying deformation operations in an X direction, a Y direction, and a Z direction to the subject depicted in the target image. There are four deformation operations: parallel movement, rotation, expansion and contraction, and shearing. On the other hand, the non-linear conversion is a process in which points each having a predetermined X coordinate, a predetermined Y coordinate, and a predetermined Z coordinate in the target image are set as node points, and at least a part of the target image is deformed in accordance with interpolation using a B-spline curve at these node points.

The blood vessel region specifying unit 11 specifies a blood vessel region by applying, for example, binarization and region growing to a medical image subjected to registration. FIG. 2 is a diagram showing an example of the blood vessel region according to the embodiment of the invention. A subject depicted in a medical image including a blood vessel region V1 shown in FIG. 2 is different from a subject depicted in a medical image including a blood vessel region V2 shown in FIG. 2. In addition, both the blood vessel region V1 and the blood vessel region V2 are three-dimensional regions in which a blood vessel of the subject is depicted.

The feature line deriving unit 12 executes, for each subject, a process of deriving a feature line that connects feature points included in each of a plurality of figures included in the blood vessel region and that is along the blood vessel region. A figure included in the blood vessel region referred to here is, for example, a sphere or a regular polyhedron that is determined according to a certain rule for the blood vessel region. In addition, the feature points are points determined according to a certain rule for the figure included in the blood vessel region. In the following description, a sphere inscribed in the blood vessel region will be described as an example of such a figure.

FIG. 3 is a diagram showing an example of a plurality of the spheres inscribed in the blood vessel region and a feature line connecting centers of the spheres according to the embodiment of the invention. The plurality of spheres shown in FIG. 3 are examples of the above-described plurality of figures.

For example, as shown in FIG. 3, the feature line deriving unit 12 determines a sphere C101, a sphere C102, a sphere C103, a sphere C104, a sphere C105, a sphere C106, a sphere C107, a sphere C108, a sphere C109, a sphere C110, and a sphere C111 that are inscribed in the blood vessel region V1. The feature line deriving unit 12 derives a feature line L1 connecting centers of these spheres indicated by black dots in FIG. 3. As shown in FIG. 3, the feature line L1 is a line along the blood vessel region V1, passes through the inside of the blood vessel region V1, and does not pass through the outside of the blood vessel region V1. The centers of the spheres, indicated by the black dots in FIG. 3, are an example of the above-described feature points.

Similarly, as shown in FIG. 3, the feature line deriving unit 12 determines a sphere C201, a sphere C202, a sphere C203, a sphere C204, a sphere C205, a sphere C206, a sphere C207, a sphere C208, a sphere C209, a sphere C210, and a sphere C211 that are inscribed in the blood vessel region V2. The feature line deriving unit 12 derives a feature line L2 connecting centers of these spheres indicated by black dots in FIG. 3. As shown in FIG. 3, the feature line L2 is a line along the blood vessel region V2, passes through the inside of the blood vessel region V2, and does not pass through the outside of the blood vessel region V2. The centers of the spheres, indicated by the black dots in FIG. 3, are an example of the above-described feature points.

The branch point specifying unit 13 executes, for each subject, a process of specifying a branch point of the feature line. For example, the branch point specifying unit 13 specifies the center of the sphere C104 and the center of the sphere C109 shown in FIG. 3 as branch points of the feature line L1. Similarly, the branch point specifying unit 13 specifies the center of the sphere C204 and the center of the sphere C209 shown in FIG. 3 as branch points of the feature line L2.

Specifically, the branch point specifying unit 13 sets voxels having equal side dimensions in at least a part of the feature line and the periphery thereof, assigns "1" to the voxels through which the feature line passes, and assigns "0" to the voxels through which the feature line does not pass. Next, the branchpoint specifying unit 13 sets, as branch point candidates, the voxels in which the number of voxels to which "1" is assigned to the voxels adjacent in the x direction, the y direction, or the z direction among the voxels to which "1" is assigned is three or more. For each of the branch point candidate voxels, the branch point specifying unit 13 assigns values respectively corresponding to a distance from the branch point candidate voxel to each of the other branch point candidate voxels located within a predetermined range to the branch point candidate voxels.

FIG. 4 is a diagram illustrating an example of values assigned to the branch point candidates according to the embodiment of the invention. For example, for a voxel B of a branch point candidate shown in FIG. 4, the branch point specifying unit 13 assigns a sum of a value corresponding to a distance from the voxel B to a voxel B1 of another branch point candidate located within a predetermined range and a value corresponding to a distance from the voxel B to a voxel B2 of another branch point candidate.

For the voxel B1, the branch point specifying unit 13 calculates a sum "8" of a value "2" obtained by subtracting the number "1" of voxels separated from the voxel B in the x direction from "3", a value "3" obtained by subtracting the number "0" of voxels separated from the voxel B in the y direction from "3", and a value "3" obtained by subtracting the number "0" of voxels separated from the voxel B in the z direction from "3". In addition, for the voxel B2, the branch point specifying unit 13 calculates a sum "5" of a value "1" obtained by subtracting the number "2" of voxels separated from the voxel B in the x direction from "3", a value "1" obtained by subtracting the number "2" of voxels separated from the voxel B in the v direction from "3", and a value "3" obtained by subtracting the number "0" of voxels separated from the voxel B in the z direction from "3". The branch point specifying unit 13 assigns a sum "13" of the sum "8" and the sum "5" to the voxel B.

The branch point specifying unit 13 also executes the same process on other branch point candidate voxels such as the voxel B1 and the voxel B2, and determines a voxel having the largest sum of the assigned values as a voxel including a branch point.

The division point disposing unit 14 executes, for each subject, a process of disposing division points for line division on a line with a start point being one of two adjacent branch points on the feature line and an end point being the other branch point. FIG. 5 is a diagram showing an example of the two branch points, a line connecting the two branch points, a plurality of the division points disposed on the line, and spheres centered on these respective division points and inscribed in the blood vessel region according to the embodiment of the invention.

For example, the division point disposing unit 14 specifies a line R1 having a point P104 shown in FIG. 5 as a start point and a point P109 shown in FIG. 5 as an end point. Here, the point P104 coincides with the center of the sphere C104 shown in FIG. 3. Similarly, the point P109 coincides with the center of the sphere C109 shown in FIG. 3. In addition, the line R1 is a line that coincides with the line between the center of the sphere C104 and the center of the sphere C109 in the feature line L1 shown in FIG. 3. The division point disposing unit 14 executes a process of disposing division points on the line R1 for equally dividing the line R1. The division points referred to here are points indicated by black circles on the line R1 in FIG. 5, and may include at least one of a point coinciding with the point P104 and a point coinciding with the point P109, or may not include at least one of these two points. In the following description, a case in which the two points are included in the division points will be described as an example.

Similarly, the division point disposing unit 14 specifies a line R2 having a point P204 shown in FIG. 5 as a start point and a point P209 shown in FIG. 5 as an end point. Here, the point P204 coincides with the center of the sphere C204 shown in FIG. 3. Similarly, the point P209 coincides with the center of the sphere C209 shown in FIG. 3. In addition, the line R2 is a line that coincides with a line between the center of the sphere C204 and the center of the sphere C209 in the feature line L2 shown in FIG. 3. The division point disposing unit 14 executes a process of disposing division points on the line R2 for equally dividing the line R2. The division points referred to here are points indicated by black circles on the line R2 in FIG. 5, and may include at least one of a point coinciding with the point P204 and a point coinciding with the point P209, or may not include at least one of these two points. In the following description, a case in which the two points are included in the division points will be described as an example.

FIG. 6 is a diagram showing an example of a standard blood vessel according to the embodiment of the invention. The standard blood vessel generation unit 15 generates, for example, data indicating a standard blood vessel W shown in FIG. 6.

The standard blood vessel generation unit 15 executes, for each set of the division points having the same order counted from the start point to the end point in a plurality of subjects, a process of calculating a statistic amount of coordinates for the set of division points and setting a point whose coordinates are equal to the statistic amount as a standard point. The statistic amount referred to here is, for example, an average value and a median value.

For example, the standard blood vessel generation unit 15 calculates an average value of coordinates for a set of a division point that coincides with the point P104 that is a first point in the blood vessel region V1 in an order counted from a start point to an end point and a division point that coincides with the point P204 that is a first point in the blood vessel region V2 in an order counted from a start point to an end point. The standard blood vessel generation unit 15 sets a point P304 whose coordinates are equal to the average value as a standard point.

For example, the standard blood vessel generation unit 15 calculates an average value of coordinates for a set of a division point that coincides with the point P109 that is a sixth point in the blood vessel region V1 in the order counted from the start point to the end point and a division point that coincides with the point P209 that is a sixth point in the blood vessel region V2 in the order counted from the start point to the end point. The standard blood vessel generation unit 15 sets a point P309 whose coordinates are equal to the average value as a standard point.

Similarly, the standard blood vessel generation unit 15 also executes the same process for a set of a point that coincides with a point that is neither the first point nor the sixth point in the blood vessel region V1 in the order counted from the start point to the end point and a point that coincides with a point that is neither the first point nor the sixth point in the blood vessel region V2 in the order counted from the start point to the end point.

Next, the standard blood vessel generation unit 15 executes, for each set of the division points, a process of setting a dimension of a predetermined site of the figure including the standard point and included in the blood vessel region as a standard diameter at the standard point.

For example, the standard blood vessel generation unit 25 executes a process of setting a diameter of each of a sphere D104, a sphere D105, a sphere D106, a sphere D107, a sphere D108, and a sphere D109 that are inscribed in the blood vessel region V1 to be a standard diameter with a standard point included in the blood vessel region V1 as a center. Similarly, the standard blood vessel generation unit 25 executes a process of setting a diameter of each of a sphere D204, a sphere D205, a sphere D206, a sphere D207, a sphere D208, and a sphere D209 that are inscribed in the blood vessel region V2 to a standard diameter with a standard point included in the blood vessel region V2 as a center.

The standard blood vessel generation unit 15 generates data indicating a standard blood vessel, which is a virtual blood vessel whose diameter at the standard point is the standard diameter and which is along a standard line connecting a plurality of the standard points.

The blood vessel evaluation device 20 evaluates a blood vessel of an object based on a standard blood vessel determined by a standard line that is included in an image in which a blood vessel of a subject is depicted and that is along a blood vessel region in which the blood vessel of the subject is depicted and a standard diameter that is a dimension of a predetermined site in each of a plurality of figures including points on the standard line and included in the blood vessel region. The object referred to here is a person who receives an evaluation of his or her own blood vessel. In addition, the blood vessel evaluation device 20 acquires data indicating the standard blood vessel and data indicating the blood vessel of the object from the storage device 30 shown in FIG. 1.

For example, the blood vessel evaluation device 20 calculates a center line and a diameter of each part of a blood vessel of an object suffering from a disease and a center line and a diameter of each part of a blood vessel of a healthy object based on the standard line and the standard diameter of the standard blood vessel generated by the standard blood vessel generation device 10, and compares the blood vessel of the object suffering from the disease with the blood vessel of the healthy object.

FIG. 7 is a diagram showing an example of results of evaluating a center line of an internal carotid artery of an object suffering from a dolicoectasia and a center line of an internal carotid artery of a healthy object in a coronal plane by the blood vessel evaluation device according to the embodiment of the invention. White circles shown in FIG. 7 indicate projection onto the coronal plane of points through which the center line of the internal carotid artery of the object suffering from the dolicoectasia passes. Black circles shown in FIG. 7 indicate projection onto the coronal plane of points through which the center line of the internal carotid artery of the healthy object passes. In addition, a line segment shown in FIG. 7 represents a standard deviation of coordinates of the points through which the center line of the internal carotid artery of the healthy object passes. FIG. 7 shows that, when projected onto the coronal plane of the object, the center line of the internal carotid artery of the object suffering from the dolicoectasia relatively greatly deviates from the center line of the internal carotid artery of the healthy object.

FIG. 8 is a diagram showing an example of results of evaluating the center line of the internal carotid artery of the object suffering from the dolicoectasia and the center line of the internal carotid artery of the healthy object in a sagittal plane by the blood vessel evaluation device according to the embodiment of the invention. White circles shown in FIG. 8 indicate projection onto the sagittal plane of points through which the center line of the internal carotid artery of the object suffering from the dolicoectasia passes. Black circles shown in FIG. 8 indicate projection onto the sagittal plane of points through which the center line of the internal carotid artery of the healthy object passes. In addition, a line segment shown in FIG. 8 represents a standard deviation of coordinates of the points through which the center line of the internal carotid artery of the healthy object passes. FIG. 8 shows that, when projected onto the sagittal plane of the object, the center line of the internal carotid artery of the object suffering from the dolicoectasia relatively greatly deviates from the center line of the internal carotid artery of the healthy object.

FIG. 9 is a diagram showing an example of results of evaluating a diameter of the internal carotid artery of the object suffering from the dolicoectasia and a diameter of the internal carotid artery of the healthy object by the blood vessel evaluation device when viewed from a direction perpendicular to the coronal plane according to the embodiment of the invention. FIG. 9 indicates a diameter of an internal carotid artery E of the object suffering from the dolicoectasia and a diameter of an internal carotid artery H of the healthy object with the diameter of each sphere. FIG. 9 shows that, when viewed from the direction perpendicular to the coronal plane, the internal carotid artery E of the object suffering from the dolicoectasia is thicker as a whole than the internal carotid artery H of the healthy object, and a part of the internal carotid artery E is enlarged.

FIG. 10 is a diagram showing an example of results of evaluating the diameter of the internal carotid artery of the object suffering from the dolicoectasia and the diameter of the internal carotid artery of the healthy object by the blood vessel evaluation device when viewed from a direction perpendicular to the sagittal plane according to the embodiment of the invention. FIG. 10 indicates the diameter of the internal carotid artery E of the object suffering from the dolicoectasia and the diameter of the internal carotid artery H of the healthy object with the diameter of each sphere. FIG. 10 shows that, when viewed from the direction perpendicular to the sagittal plane, the internal carotid artery E of the object suffering from the dolicoectasia is thicker as a whole than the internal carotid artery H of the healthy object, and a part of the internal carotid artery E is enlarged.

Next, an example of a process executed by the standard blood vessel generation device according to the embodiment will be described with reference to FIG. 11. FIG. 11 is a flowchart illustrating an example of a process executed by the standard blood vessel generation device according to the embodiment of the invention.

In step S10, the blood vessel region specifying unit 11 executes, for each subject, a process of specifying a blood vessel region in which a blood vessel of the subject is depicted in an image in which the blood vessel of the subject is depicted.

In step S20, the feature line deriving unit 12 executes, for each subject, a process of deriving a feature line that connects feature points included in each of a plurality of figures included in the blood vessel region and that is along the blood vessel region.

In step S30, the branch point specifying unit 13 executes, for each subject, a process of specifying a branch point of the feature line.

In step S40, the division point disposing unit 14 executes, for each subject, a process of disposing division points for line division on a line with a start point being one of two adjacent branch points on the feature line and an end point being the other branch point.

In step S50, the standard blood vessel veneration unit 15 executes, for each set of the division points having the same order counted from the start point to the end point in a plurality of subjects, a process of calculating a statistic amount of coordinates for the set of division points and setting a point whose coordinates are equal to the statistic amount as a standard point.

In step S60, the standard blood vessel generation unit 15 executes, for each set of the division points, a process of setting a dimension of a predetermined site of the figure including the standard point and included in the blood vessel region as a standard diameter.

In step S70, the standard blood vessel generation unit 15 generates data indicating a standard blood vessel, which is a virtual blood vessel whose diameter at the standard point is the standard diameter and which is along a standard line connecting a plurality of the standard points.

The standard blood vessel generation device 10 and the blood vessel evaluation device 20 according to the embodiment are described above. The standard blood vessel generation device 10 includes the blood vessel region specifying unit 11, the feature line deriving unit 12, the branch point specifying unit 13, the division point disposing unit 14, and the standard blood vessel generation unit 15.

The blood vessel region specifying unit 11 executes, for each subject, the process of specifying the blood vessel region in which the blood vessel of the subject is depicted in the image in which the blood vessel of the subject is depicted. The feature line deriving unit 12 executes, for each subject, the process of deriving the feature line that connects the feature points included in each of the plurality of figures included in the blood vessel region and that is along the blood vessel region. The branch point specifying unit 13 executes, for each subject, the process of specifying the branch point of the feature line. The division point disposing unit 14 executes, for each subject, the process of disposing the division points for line division on the line with the start point being one of two adjacent branch points on the feature line and the end point being the other branch point.

The standard blood vessel generation unit 15 executes, for each subject, the process of calculating the statistic amount of the coordinates for a set of division points having the same order counted from the start point to the end point in a plurality of subjects and setting the point whose coordinates are equal to the statistic amount as the standard point. Next, the standard blood vessel generation unit 15 executes, for each set of the division points, the process of setting the dimension of the predetermined site of the figure including the standard point and included in the blood vessel region as the standard diameter. The standard blood vessel generation unit 15 generates the data indicating the standard blood vessel, which is the virtual blood vessel whose diameter at the standard point is the standard diameter and which is along the standard line connecting the plurality of standard points.

Accordingly, the standard blood vessel generation unit 15 can overcome a problem of a personal difference in a shape of a blood vessel and generate a standard blood vessel, which is a reference blood vessel suitable for specifying the blood vessel shape. In addition, the standard blood vessel generated by the standard blood vessel generation device 10 is a common reference blood vessel in a case of evaluating a shape of a blood vessel having a relatively large personal difference, and thus can be used for research and development of medical devices, efficient prevention, diagnosis, treatment of diseases, and the like. Further, the standard blood vessel generated by the standard blood vessel generation device 10 is determined by the standard line and standard diameter, and thus the standard blood vessel can be a reference clearer than an existence probability distribution of a blood vessel in specifying a shape of a blood vessel. In addition, the data indicating the standard blood vessel generated by the standard blood vessel veneration device 10 is different from data regarding a blood vessel of an individual, and thus it is easy to handle the data indicating the standard blood vessel in consideration of the logical viewpoint.

The standard blood vessel generation device 10 may execute a process of specifying a blood vessel region in which a blood vessel of a subject is depicted in an image subjected to registration with respect to a reference image having a reference coordinate system. Accordingly, the standard blood vessel generation device 10 can unify an image to be used for generating a standard blood vessel in the coordinate system of the reference image, and generate data indicating a more accurate standard blood vessel.

The standard blood vessel generation device 10 may execute a process of disposing the division points on the line for equally dividing the line. Accordingly, the standard blood vessel generation device 10 can generate the data indicating the more accurate standard blood vessel by using a point that is highly likely to correspond between different subjects as a reference point.

The blood vessel evaluation device 20 evaluates the blood vessel of the object based on the standard blood vessel determined by the standard line that is included in the image in which the blood vessel of the subject is depicted and that is along the blood vessel region in which the blood vessel of the subject is depicted and the standard diameter that is the dimension of the predetermined site in each of the plurality of figures including the points on the standard line and included in the blood vessel region. Accordingly, the blood vessel evaluation device 20 can execute not only a qualitative evaluation but also a quantitative evaluation of the blood vessel of the object based on the standard blood vessel that is the reference blood vessel suitable for specifying the shape of the blood vessel.

Next, an example of a standard blood vessel generation device according to another embodiment will be described with reference to FIGS. 12 to 20. FIG. 12 is a diagram showing an example of a functional configuration of the standard blood vessel generation device according to the other embodiment of the invention. In the following description, the description related to the content that overlaps with the above-described embodiment will be appropriately omitted.

As shown in FIG. 12, a standard blood vessel generation device 40 includes an end point specifying unit 131 and a feature line classification unit 132 in addition to the blood vessel region specifying unit 11, the feature line deriving unit 12, the branch point specifying unit 13, the division point disposing unit 14, and the standard blood vessel generation unit 15.

The end point specifying unit 131 executes, for each subject, a process of specifying an end point of a feature line. The end point referred to here includes an end point that is generated when a blood vessel region has a thickness equal to or less than a certain thickness and the feature line cannot be determined, and an end point that is generated when the blood vessel region is interrupted at an end portion of an image.

For example, the end point specifying unit 131 sets voxels having equal side dimensions in at least a part of a feature line and a periphery thereof, assigns "1" to the voxels through which the feature line passes, and assigns "0" to the voxels through which the feature line does not pass. Next, the end point specifying unit 131 selects, as a starting point, any voxel to which "1" is assigned in a three-dimensional space in which an x direction, a y direction, and a z direction are defined. The end point specifying unit 131 traces adjacent voxels in order starting from the voxel, and specifies, as an end point, a voxel from which the adjacent voxels cannot be traced in the three-dimensional space. In addition, the adjacent voxels referred to here mean a voxel that is present at a position moved by one voxel in at least one direction of the x direction, the y direction, and the z direction in the three-dimensional space.

The feature line classification unit 132 executes, for each subject, a process of determining a category to which a connection structure of a feature line depicted in an image belongs, based on a connection relation between branch points on the feature line. In addition, the feature line classification unit 132 may execute, for each subject, a process of determining a category to which a blood vessel depicted in the image belongs, based on not only the connection relation between the branch points on the feature line, but also a connection relation between the end point and a feature point on the feature line.

FIG. 13 is a diagram showing an example of a blood vessel according to the other embodiment of the invention. Specifically, FIG. 13 shows an example of a blood vessel in which no posterior communicating artery is formed. When the blood vessel shown in FIG. 13 is depicted in an image, the branch point specifying unit 13 specifies, for example, points "1" and "5" circled in FIG. 13 as branch points of a feature line. When the blood vessel shown in FIG. 13 is depicted in the image, the end point specifying unit 131 specifies, for example, points "3" and "6" circled in FIG. 13 as end points of the feature line.

FIG. 14 is a diagram showing an example of a matrix indicating a connection relation between the branch points and the end points on the feature line of the blood vessel shown in FIG. 13. Numbers shown at an upper end and a left end in FIG. 14 indicate the branch points or the end points shown in FIG. 13. In addition, a white circle shown in FIG. 14 indicates that a row point and a column point that are indicated by the White circle are connected to each other by the feature line. For example, a white circle shown in a first row and a third column in FIG. 14 indicates that the branch point "1" and the end point "3" shown in FIG. 13 are connected to each other by the feature line. In addition, a white circle shown in a fourth row and a sixth column in FIG. 14 indicates that the branch point "5" and the end point "6" shown in FIG. 13 are connected to each other by the feature line.

FIG. 15 is a diagram showing an example of a blood vessel according to the other embodiment of the invention. Specifically, FIG. 15 shows an example of a blood vessel published in a general anatomy textbook. When the blood vessel shown in FIG. 15 is depicted in an image, the branch point specifying unit 13 specifies, for example, points "1", "2", "4", and "5" circled in FIG. 15 as branch points of a feature line. When the blood vessel shown in FIG. 15 is depicted in the image, the end point specifying unit 131 specifies, for example, points "3" and "6" circled in FIG. 15 as end points of the feature line.

FIG. 16 is a diagram showing an example of a matrix indicating a connection relation between the branch points and the end points on the feature line of the blood vessel shown in FIG. 15. Numbers shown at an upper end and a left end in FIG. 16 indicate the branch points or the end points shown in FIG. 15. In addition, a white circle shown in FIG. 16 indicates that a row point and a column point that are indicated by the white circle are connected to each other by the feature line. For example, a white circle shown in a first row and a second column in FIG. 16 indicates that the branch point "1" and the branch point "2" shown in FIG. 15 are connected to each other by the feature line. In addition, a white circle shown in a fifth row and a sixth column in FIG. 16 indicates that the branch point "5" and the end point "6" shown in FIG. 15 are connected to each other by the feature line.

FIG. 17 is a diagram showing an example of a blood vessel according to the other embodiment of the invention. Specifically, FIG. 17 shows an example of a blood vessel in which a posterior communicating artery is longer than a posterior inferior cerebellar artery. When the blood vessel shown in FIG. 17 is depicted in an image, the branch point specifying unit 13 specifies, for example, points "1", "4", and "5" circled in FIG. 17 as branch points of a feature line. When the blood vessel shown in FIG. 17 is depicted in the image, the end point specifying unit 131 specifies, for example, points "3" and "6" circled in FIG. 17 as end points of the feature line.

FIG. 18 is a diagram showing an example of a matrix indicating a connection relation between the branch points and the end points on the feature line of the blood vessel shown in FIG. 17. Numbers shown at an upper end and a left end in FIG. 18 indicate the branch points or the end points shown in FIG. 17. In addition, a white circle shown in FIG. 18 indicates that a row point and a column point that are indicated by the white circle are connected to each other by the feature line. For example, a white circle shown in a third row and a fourth column in FIG. 18 indicates that the end point "3" and the branch point "4" shown in FIG. 17 are connected to each other by the feature line. In addition, a white circle shown in a fifth row and a sixth column in FIG. 18 indicates that the branch point "5" and the end point "6" shown in FIG. 17 are connected to each other by the feature line.

The division point disposing unit 14 executes, for at least two feature lines determined to belong to the same category by the feature line classification unit 132, a process of disposing division points on a line with a start point being one of two adjacent branch points on the feature line and an end point being the other branch point. The standard blood vessel generation unit 15 executes a process of generating data indicating a standard blood vessel based on at least two feature lines determined to belong to the same category by the feature line classification unit 132.

The standard blood vessel generation device 40 according to the other embodiment is described above. The standard blood vessel generation device 40 includes the end point specifying unit 131 and the feature line classification unit 132. The end point specifying unit 131 executes, for each subject, the process of specifying the end point of the feature line. The feature line classification unit 132 executes, for each subject, the process of determining the category to which the connection structure of the feature line depicted in the image belongs, based on the connection relation between the branch points on the feature line. The standard blood vessel generation device 40 executes a process of disposing the division points for at least two feature lines determined to belong to the same category by the feature line classification unit 132, and generates data indicating a standard blood vessel.

Accordingly, the standard blood vessel generation device 40 can further generate a detailed standard blood vessel for each blood vessel category based only on at least two subjects who have blood vessels belonging to the same category.

The feature line classification unit 132 executes, for each subject, a process of determining the category to which the connection structure of the feature line depicted in the image belongs, based on not only the connection relation between the branch points on the feature line, but also the connection relation between the end point and the feature point on the feature line.

Accordingly, the standard blood vessel generation device 40 can further improve an accuracy of the process of determining the category to which the blood vessel depicted in the image belongs.

Next, a specific example of an effect exhibited by the standard blood vessel generation device according to the other embodiment will be described with reference to FIGS. 19 and 20.

FIG. 19 is a diagram showing an example of a standard blood vessel generated by the standard blood vessel generation device based on blood vessels of a plurality of subjects classified into a left and right independent type when the posterior communicating artery is considered according to the other embodiment of the invention. An average diameter of the standard blood vessel shown in FIG. 19 is 4.03±0.52 mm. The standard blood vessel generation device 40 can generate a detailed standard blood vessel for each blood vessel category shown in FIG. 19 based only on the subject having the blood vessels classified into the left and right independent type when the posterior communicating artery is considered.

FIG. 20 is a diagram showing an example of a standard blood vessel generated by the standard blood vessel generation device based on blood vessels of a plurality of subjects classified into a left and right coupled type when the posterior communicating artery is considered according to the other embodiment of the invention. An average diameter of the standard blood vessel shown in FIG. 20 is 3.45±0.49 mm. The standard blood vessel generation device 40 can generate a detailed standard blood vessel for each blood vessel category shown in FIG. 20 based only on the subjects having the blood vessels classified into the left and right coupled type when the posterior communicating artery is considered.

In the above-described embodiments, a case in which the subject is a human head and the blood vessel is an artery in a brain is described as an example, and the invention is not limited thereto. The subject may be a site other than the human head, or a part of a body of an animal. Examples of the site other than the human head include a heart, limbs, and eyeballs. The above-described medical image is preferably the above-described MRA image, CTA image, or ultrasonic image when the subject is the heart or the limbs. In addition, when the subject is the eyeballs, the above-described medical image may be, for example, the above-described MRA image, CTA image, or ultrasonic image, or may be a fundus three-dimensional image captured by an examination using an optical coherence tomography (OCT). Further, the blood vessel may be a vein.

At least a part of functions of the standard blood vessel generation device 10 and at least a part of functions of the blood vessel evaluation device 20 may be implemented by hardware including circuitry such as a large scale integration (LSI), an application specific integrated circuit (ASIC), a field-programmable gate array (FPGA), and a graphics processing unit (GPU).

At least a part of the functions of the standard blood vessel generation device 10 and at least a part of the functions of the blood vessel evaluation device 20 may be implemented through cooperation of the hardware and software. The software may be stored in, for example, a storage device including a non-transitory storage medium, and may be read and executed by the hardware. The storage device is, for example, a hard disk drive (HDD) and a solid state drive (SSD). Alternatively, the software may be stored in a storage device including a removable non-transitory storage medium, and may be read and executed by the hardware. The storage device is, for example, a DVD and a CD-ROM.

In the above-described embodiments, a case in which the standard blood vessel generation device 10 includes the blood vessel region specifying unit 11, the feature line deriving unit 12, the branch point specifying unit 13, the end point specifying unit 131, the feature line classification unit 132, the division point disposing unit 14, and the standard blood vessel generation unit 15 is described as an example, and the invention is not limited thereto. For example, a part of the functions of the standard blood vessel generation device 10 may be implemented by specific hardware, and the other part of the functions of the standard blood vessel generation device 10 may be implemented by another hardware. In addition, for example, a part of the functions of the standard blood vessel generation device 10 may be implemented by specific hardware and software, and the other part of the functions of the standard blood vessel generation device 10 may be implemented by the other hardware and software.

Although the embodiments of the invention are described above with reference to the drawings, the embodiment of the invention is not limited to the embodiments described above, and at least one of various modifications, substitutions, and changes in design can be added without departing from the scope of the invention.

REFERENCE SIGN LIST 10, 40 standard blood vessel generation device
11 blood vessel region specifying unit
12 feature line deriving unit
13 branch point specifying unit
131 end point specifying unit
132 feature line classification unit
14 division point disposing unit
15 standard blood vessel generation unit
20 blood vessel evaluation device 30 storage device
NW network
The invention claimed is:

1. A standard blood vessel generation device comprising:
a blood vessel region specifying unit configured to execute, for each subject, a process of specifying a blood vessel region in which a blood vessel of the subject is depicted in an image in which the blood vessel of the subject is depicted;
a feature line deriving unit configured to execute, for each subject, a process of deriving a feature line that connects feature points included in each of a plurality of figures included in the blood vessel region and that is along the blood vessel region;
a branch point specifying unit configured to execute, for each subject, a process of specifying a branch point of the feature line;
a division point disposing unit configured to execute, for each subject, a process of disposing division points for line division on a line with a start point being one of two adjacent branch points on the feature line and an end point being the other branch point; and
a standard blood vessel generation unit configured to execute, for each set of the division points having the same order counted from the start point to the end point in a plurality of the subjects, a process of calculating a statistic amount of coordinates for the set of the division points and setting a point whose coordinates are equal to the statistic amount as a standard point, and a process of setting a dimension of a predetermined site in the figure including the standard point and included in the blood vessel region as a standard diameter, and generate data indicating a three-dimensional standard blood vessel that is a virtual blood vessel whose diameter at the standard point is the standard diameter and that is along a standard line connecting a plurality of the standard points.

2. The standard blood vessel generation device according to claim 1, wherein
the blood vessel region specifying unit is configured to execute the process of specifying the blood vessel region in which the blood vessel of the subject is depicted in the image subjected to registration with respect to a reference image having a reference coordinate system.

3. The standard blood vessel generation device according to claim 1, wherein
the feature line deriving unit is configured to execute the process of deriving the feature line connecting centers of a plurality of spheres inscribed in the blood vessel region.

4. The standard blood vessel generation device according to claim 1, wherein
the division point disposing unit is configured to execute the process of disposing the division points on the line for equally dividing the line.

5. The standard blood vessel generation device according to claim 1, wherein
the standard blood vessel generation unit is configured to generate, as the three-dimensional standard blood vessel, the data indicating the virtual blood vessel having the diameter at the standard point equal to a diameter of a sphere inscribed in the blood vessel region.

6. The standard blood vessel generation device according to claim 1, further comprising:
a feature line classification unit configured to execute, for each subject, a process of determining a category to which a connection structure of the feature line depicted in the image belongs, based on a connection relation between the branch points on the feature line, wherein the division point disposing unit is configured to execute the process of disposing the division points on the line for at least two blood vessels determined to belong to the same category by the feature line classification unit, and the standard blood vessel generation unit is configured to execute the process of generating the data indicating the three-dimensional standard blood vessel based on at least two blood vessels determined to belong to the same category by the feature line classification unit.

7. The standard blood vessel generation device according to claim 6, further comprising:

an end point specifying unit configured to execute, for each subject, a process of specifying an end point of the feature line, wherein the feature line classification unit is configured to execute, for each subject, the process of determining the category to which the blood vessel depicted in the image belongs, based on a connection relation between the end point of the feature line specified by the end point specifying unit and the nearest branch point or other end point on the feature line.

8. A system comprising the standard blood vessel generation device according to claim 1 and a blood vessel evaluation device, wherein the subject is a subject suffering from a disease or a healthy subject, and wherein a blood vessel of the subject suffering from the disease is evaluated based on the standard line and the standard diameter of the three dimensional standard blood vessel generated by the standard blood vessel generation device according to claim 1 by comparing the blood vessel of the subject suffering from the disease with a standard blood vessel generated based on images from a plurality of the healthy subjects.

9. A non-transitory storage medium storing a program causing a computer to implement:

executing, for each subject, a process of specifying a blood vessel region in which a blood vessel of the subject is depicted in an image in which the blood vessel of the subject is depicted;

executing, for each subject, a process of deriving a feature line that connects feature points included in each of a plurality of figures included in the blood vessel region and that is along the blood vessel region;

executing, for each subject, a process of specifying a branch point of the feature line;

executing, for each subject, a process of disposing division points for line division on a line with a start point being one of two adjacent branch points on the feature line and an end point being the other branch point; and executing, for each set of the division points having the same order counted from the start point to the end point in a plurality of the subjects, a process of calculating a statistic amount of coordinates for the set of the division points and setting a point whose coordinates are equal to the statistic amount as a standard point, and a process of setting a dimension of a predetermined site in the figure including the standard point and included in the blood vessel region as a standard diameter, and generating data indicating a three-dimensional standard blood vessel that is a virtual blood vessel whose diameter at the standard point is the standard diameter and that is along a standard line connecting a plurality of the standard points.

10. A non-transitory storage medium storing a program, wherein the subject is a subject suffering from a disease or a healthy subject, causing a computer to implement:

evaluating a blood vessel of the subject suffering from the disease based on the standard line and the standard diameter of the three-dimensional standard blood vessel generated by the standard blood vessel generation device according to claim 1 by comparing the blood vessel of the subject suffering from the disease with a standard blood vessel generated based on images from a plurality of the healthy subjects.

11. A standard blood vessel generation method comprising:

a blood vessel region specifying step of executing, for each subject, a process of specifying a blood vessel region in which a blood vessel of the subject is depicted in an image in which the blood vessel of the subject is depicted;

a feature line deriving step of executing, for each subject, a process of deriving a feature line that connects feature points included in each of a plurality of figures included in the blood vessel region and that is along the blood vessel region;

a branch point specifying step of executing, for each subject, a process of specifying a branch point of the feature line;

a division point disposing step of executing, for each subject, a process of disposing division points for line division on a line with a start point being one of two adjacent branch points on the feature line and an end point being the other branch point; and a standard blood vessel generation step of executing, for each set of the division points having the same order counted from the start point to the end point in a plurality of the subjects, a process of calculating a statistic amount of coordinates for the set of the division points and setting a point whose coordinates are equal to the statistic amount as a standard point, and a process of setting a dimension of a predetermined site in the figure including the standard point and included in the blood vessel region as a standard diameter, and generating data indicating a three-dimensional standard blood vessel that is a virtual blood vessel whose diameter at the standard point is the standard diameter and that is along a standard line connecting a plurality of the standard points.

12. A blood vessel evaluation method, wherein the subject is a subject suffering from a disease or a healthy subject, the method comprising:

evaluating a blood vessel of the subject suffering from the disease is based on the standard line and the standard diameter of the three-dimensional standard blood vessel generated by the standard blood vessel generation device according to claim 1 by comparing the blood vessel of the subject suffering from the disease with a standard blood vessel generated based on images from a plurality of the healthy subjects.

* * * * *